(12) United States Patent
Abri et al.

(10) Patent No.: US 9,271,795 B2
(45) Date of Patent: Mar. 1, 2016

(54) MEDICAL WORKPLACE

(71) Applicant: Karl Storz GmbH & Co. KG, Tuttlingen (DE)

(72) Inventors: Omid Abri, Berlin (DE); Svenia Karge, Berlin (DE); Thorsten Karge, Berlin (DE); Julian Verkin, Hohen Neuendorf (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 0 days.

(21) Appl. No.: 14/019,265

(22) Filed: Sep. 5, 2013

(65) Prior Publication Data
US 2014/0072395 A1    Mar. 13, 2014

(30) Foreign Application Priority Data
Sep. 5, 2012    (DE) .......................... 10 2012 108 263

(51) Int. Cl.
| | |
|---|---|
| *A61B 19/00* | (2006.01) |
| *A61G 15/14* | (2006.01) |
| *A61G 12/00* | (2006.01) |
| *A61G 10/00* | (2006.01) |

(52) U.S. Cl.
CPC ................ *A61B 19/00* (2013.01); *A61G 10/00* (2013.01); *A61G 12/004* (2013.01); *A61G 12/007* (2013.01); *A61G 15/14* (2013.01)

(58) Field of Classification Search
CPC ..... A61B 19/00; A61G 15/14; A61G 12/007; A61G 12/004; A61G 19/00; A61G 10/00
USPC ........... 312/209, 114, 117, 198, 239; 108/28, 108/42, 50.01, 50.02
See application file for complete search history.

(56) References Cited

U.S. PATENT DOCUMENTS

| | | | | |
|---|---|---|---|---|
| 3,267,881 | A * | 8/1966 | Saggione | 108/59 |
| 3,922,788 | A | 12/1975 | Rota | |
| 3,931,452 | A * | 1/1976 | Nilsson | 174/491 |
| 4,332,557 | A * | 6/1982 | Watanabe | 433/77 |
| 4,646,211 | A | 2/1987 | Gallant et al. | |
| 4,738,369 | A | 4/1988 | Desjardins | |
| 4,863,223 | A * | 9/1989 | Weissenbach et al. | 312/209 |
| 5,037,164 | A * | 8/1991 | Weissenbach et al. | 108/50.02 |
| 5,615,936 | A * | 4/1997 | Simmons et al. | 312/238 |
| 6,033,045 | A * | 3/2000 | Roberts et al. | 312/194 |
| 6,170,102 | B1 * | 1/2001 | Kreuzer | 5/601 |
| 6,349,436 | B1 * | 2/2002 | Kreuzer | 5/600 |
| 6,463,701 | B1 * | 10/2002 | Baloga et al. | 52/29 |

(Continued)

FOREIGN PATENT DOCUMENTS

| | | |
|---|---|---|
| DE | 1947803 U | 10/1966 |
| DE | 7123181 U | 11/1971 |

(Continued)

OTHER PUBLICATIONS

FR2693103 Translation.pdf, machine translation obtained from ESPACENET on May 1, 2014.*

*Primary Examiner* — Andrew Roersma
(74) *Attorney, Agent, or Firm* — Whitmyer IP Group LLC

(57) ABSTRACT

A medical workstation includes a position provided for medical personnel during a medical activity on a patient, and storage units for receiving medical instruments or tools. The storage units are arranged in the shape of an arc of a circle around the position provided for medical personnel.

18 Claims, 6 Drawing Sheets

(56) References Cited

U.S. PATENT DOCUMENTS

| | | | |
|---|---|---|---|
| 6,739,096 B2* | 5/2004 | Feldpausch et al. | 52/36.1 |
| 7,644,898 B2 | 1/2010 | White et al. | |
| 7,735,266 B2* | 6/2010 | Gallant et al. | 52/36.4 |
| 7,793,907 B2* | 9/2010 | Woodward et al. | 248/317 |
| 2004/0199996 A1* | 10/2004 | Newkirk et al. | 5/81.1 R |
| 2007/0176060 A1 | 8/2007 | White et al. | |

FOREIGN PATENT DOCUMENTS

| | | | |
|---|---|---|---|
| DE | 7132009 U | 2/1972 | |
| DE | 2141990 A1 | 2/1973 | |
| DE | 2141991 A1 | 2/1973 | |
| DE | 2220068 A1 | 11/1973 | |
| DE | 2428169 A1 | 1/1975 | |
| DE | 8526645 U1 | 11/1985 | |
| DE | 3541017 A1 | 6/1986 | |
| DE | 8716928 U1 | 4/1989 | |
| DE | 29505059 U1 | 5/1995 | |
| DE | 29600647 U1 | 7/1996 | |
| DE | 19807242 A1 | 8/1999 | |
| DE | 19807243 A1 | 8/1999 | |
| DE | 20002305 U1 | 4/2000 | |
| DE | 102007051038 A1 | 4/2009 | |
| FR | 2050560 A5 | 4/1971 | |
| FR | 2693103 A1 | 1/1994 | |
| WO | WO0119216 A2 * | 3/2001 | A47B 87/00 |
| WO | 02096335 A2 | 12/2002 | |
| WO | 02096340 A1 | 12/2002 | |

* cited by examiner

US 9,271,795 B2

MEDICAL WORKPLACE

FIELD OF THE INVENTION

The present invention relates to a medical workstation, in particular to a medical workstation within a medical practice.

BACKGROUND OF THE INVENTION

For the medically, ergonomically and economically optimal set-up of operating theaters and for the integration of the functions thereof, extensively developed concepts and complex technical approaches are available that have already proven their worth. Compared to an operating theater, a medical workstation within a medical practice is generally the scene of a considerably smaller variety of medical procedures, which are also much less complex. However, the set-up of a medical workstation within a medical practice is by no means routine from the medical, ergonomic and economic points of view.

It is astonishing that the vast majority of medical workstations within medical practices are still being developed and produced on an individual basis and in a manner specific to the customer. This means constantly re-inventing the wheel, and knowledge and experience that has already been acquired is not systematically and comprehensively recorded and evaluated in order to be used in subsequent developments. This results in highly individual medical workstations which reflect the esthetic requirements of the doctors and the skilled work involved in their production, but which in many cases are not optimal from the medical, ergonomic or economic point of view.

The prevailing individualized production of medical workstations generally rules out meaningful but technically complex solutions, since the development and realization of these is uneconomic for single items. Moreover, individually configured medical workstations are generally not set up such that subsequent modifications or additions can be made with minimal outlay.

Proceeding from this situation, the applicant has set itself the object of developing concepts, components and technical solutions which, from medical, ergonomic and economic aspects, simultaneously permit clear improvements, a reduction in costs through serial production, and meaningful individualization to the extent required by physicians. Because of the very different requirements, adopting concepts that were developed for operating theaters is possible at best to a limited extent.

FR 2 050 560 describes a functional unit for a dentist. A position for medical personnel is provided in the inside of a cylindrical or semicircular furniture item.

DE 2 141 991 describes a dental facility for dental practice. A running track for an instrument carriage is arranged on a circular cabinet unit with circular front. The position provided for the patient is arranged at the center point of the circular cabinet wall.

DE 1 947 803 describes a device with ophthalmic examination instruments. A work surface has the shape of a circular ring section, at the center of which a patient's chair is arranged.

German utility model 7132009 describes a dental facility for a dental practice. A track is arranged on a cabinet wall arranged in the shape of a circle around the treatment chair. A carriage for instruments is movable on the track. The position provided for the patient is arranged at the center point of the circular cabinet wall.

FR 2 693 103 describes a furniture item for a dental practice. The front of the semicircular furniture item is cylindrical with a vertical axis of symmetry. A chair for a patient is arranged at the center of a semicircular furniture item.

DE 198 07 242 A1 describes a medical/technical system workstation. An administration unit for medical appliances is arranged movably on rails of a patient support panel.

DE 198 07 243A1 describes a medical workstation. An appliance center for surgical and diagnostic appliances is guided on rails in order to permit a circular adjustment.

DE 200 02 305 U1 describes a modular furniture arrangement for medical practices. Several modules are arranged in a U-shape around a patient bench.

DE 295 05 059 describes a treatment facility for a medical/dental practice. An appliance tray and an instrument panel are mounted pivotably.

DE 296 00 647 describes a work surface below which guiding rails and running rails are placed, via which furniture elements can be driven laterally.

German utility model 7123181 describes a dental facility for a dental practice, comprising a drilling and treatment unit in the shape of a driveable carriage. The positions provided for medical personnel and patients are arranged inside a rectangularly U-shaped arrangement of cabinet units.

DE 2 220 068 describes a dental appliance cabinet of which the contour is U-shaped.

US 2007/0176060 (later published as U.S. Pat. No. 7,644,898) describes a medical boom with moveable arms for holding video displays.

SUMMARY OF THE INVENTION

An object of the present invention is to create an improved medical workstation.

This object is achieved by the subject matter of the independent claims.

Developments are set forth in the dependent claims.

A medical workstation comprises storage units for receiving medical instruments or tools, and a transport rail for holding an instrument carrier that is movable along the transport rail, wherein the transport rail has a loading area, an unloading area and, between the loading area and the unloading area, a use area, wherein the use area is arranged in a room area above the storage units.

The medical workstation is in particular a medical workstation within a medical practice of a general practitioner, within a medical centre, or within the outpatient area of a clinic. However, the medical workstation in particular is not an operating theater, in which the arrangement of storage units is generally irrelevant anyway because of other procedures and because of the presence of medical assistants who, for example, hand over instruments and take them back. The medical workstation can also differ very greatly from an operating theater in terms of further properties and features described below.

The position provided for medical personnel, in particular for a doctor, during a medical activity on a patient is in particular defined by a seat area for the medical personnel on a stool or other seat furniture. Alternatively, the position provided for medical personnel during a medical activity on a patient can be a standing place provided for the medical personnel.

The storage units are provided and designed for receiving medical instruments, medicaments, disposable items and/or other tools. Moreover, the storage units can be designed for receiving soiled or unsterile instruments, after use thereof, and waste material. Beside or between the storage units, medical appliances can be arranged in the same arc of a circle. In particular, cabinet-shaped appliances for the provision of gas, light, and mechanical or electrical power for medical instruments can form, together with the storage units, a horizontal arc of a circle.

In a medical workstation of the kind described here, the storage units are arranged in particular in the shape of an arc of a circle around the position provided for medical personnel.

A medical workstation comprises a position provided for medical personnel during a medical activity on a patient, and storage units for receiving medical instruments or tools, wherein the storage units are arranged in the shape of an arc of a circle around the position provided for medical personnel.

The arrangement of storage units, and optionally of medical appliances, in the shape of an arc of a circle has the effect that all of the storage units and appliances can be reached equally easily from the position provided for the medical personnel. The storage units can have rectangular contours. However, for esthetic aspects and for avoiding dead angles that are difficult to clean, storage units with trapezoid contours and with contours in the shape of segments of an arc of a circle can be advantageous. However, the design and especially the production of storage units with trapezoid contours, and in particular with contours in the shape of segments of an arc of a circle, are much more complicated than the design and production of conventional storage units with a square shape. It is presumably also for this reason that an arrangement of storage units, and optionally of appliances, in the shape of an arc of a circle was apparently not previously considered.

In a medical workstation of the kind described here, front faces of the storage units form areas of a circular cylindrical jacket surface, of which the axis of symmetry is vertical, and on the axis of symmetry of which lies the position provided for medical personnel.

In particular, all or substantially all of the vertical front faces of the storage units form areas of a circular cylindrical jacket surface. The front faces form areas of a circular cylindrical jacket surface within the meaning of the present description even if, for example for reasons relating to esthetics or to manufacturing technology, they deviate from the ideal circular cylindrical jacket shape slightly (for example by a few percent, in particular at most 10%, of the diameter of the circular cylindrical jacket). If the position provided for medical personnel is defined by a seat surface, the position then lies in particular on the axis of the circular cylindrical jacket, when the axis passes through the seat surface at the center thereof or at another point, i.e. when the edge of the seat surface surrounds the axis of the cylinder jacket.

The circular cylindrical jacket surface has in particular a diameter of between 1.5 meters and 2.0 meters, for example 1.8 meters. This diameter has proven ideal in many situations and for many doctors since, on the one hand, it provides sufficient range of movement between the storage units and, on the other hand, ensures that these storage units can be easily reached from the position provided for medical personnel.

In a medical workstation of the kind described here, a position provided for a patient during a medical activity is in particular arranged in the arc of a circle formed by the storage units.

In particular, a seat or a bed for a patient is arranged inside the arc of a circle formed by the storage units and optionally by medical appliances. Alternatively, only the relevant area or body part of the patient is arranged in the arc of a circle, for example the head in the case of a dental or orthodontic or ENT practice. If the patient, or the relevant area of the patient, and the storage units are arranged in the shape of an arc of a circle around the position provided for medical personnel, the medical personnel can reach the patient and the storage units more or less equally easily.

A medical workstation of the kind described here also comprises in particular a transport rail for holding an instrument carrier that is movable along the transport rail, wherein the transport rail has a loading area and an unloading area and, between the loading area and the unloading area, a use area, wherein the use area is arranged in a room area above the storage units.

The transport rail is in particular arranged horizontally in order to permit a horizontal movement of the one or more instrument carriers. One or more instrument carriers can be moved manually or by motor along the transport rail. In addition to one or more instrument carriers, it is also possible for medical appliances, trays, waste containers and/or other devices to be moved along the transport rail.

The loading area and/or the unloading area can be arranged in an area of the room that is partly or wholly separate from the medical workstation. In particular, partition walls can be provided between the position provided for a patient and the loading area and/or between the position provided for a patient and the unloading area. The loading area and the unloading area can be arranged in the same or substantially the same room area or in two adjoining room areas. Alternatively, the loading area and the unloading area can be arranged in two room areas at a distance from each other. In particular, the medical workstation is arranged between the room area in which the loading area is arranged and the room area in which the unloading area is arranged.

The transport rail permits the equipping of a first instrument carrier with sterile instruments and/or disposable items in the loading area, the emptying of a second instrument carrier in the unloading area, and at the same time the use of a third instrument carrier and of instruments on the third instrument carrier in the use area, without these three procedures impeding one another. The required time interval between medical activities on different patients can thus be made shorter.

In a medical workstation of the kind described here, the transport rail is in particular arranged in a horizontal plane above and at a distance from the storage units.

In a medical workstation with a transport rail, as it is described here, the use area is arc-shaped in particular.

In particular, the use area is designed in the shape of an arc of a circle, or for mobility of the instrument carrier along an arc of a circle, wherein the center point of the curvature is arranged on or vertically above the position provided for medical personnel during a medical activity on a patient.

In the case of a use area designed in the shape of an arc, in particular in the shape of an arc of a circle, an instrument carrier is equally accessible, from the position provided for medical personnel, at all locations on the transport rail within the use area.

In a medical workstation with a transport rail, as it is described here, at least either the loading area or the unloading area is at a greater distance from the position provided for medical personnel than is the use area.

A medical workstation, as it is described here, also comprises in particular an arc-shaped support rail for holding an appliance which is provided for use by medical personnel and is movable along the support rail.

The arc-shaped support rail is in particular designed in the shape of an arc of a circle, or for holding an appliance at one of several alternative locations lying on an arc of a circle. The arc-shaped support rail can hold a plurality of appliances. Examples of appliances held by the support rail are a monitor or display screen, or another display device, a holding arm for an endoscope, for an exoscope, for a microscope or for another medical instrument or appliance, a holding arm for a user interface of a medical appliance.

The one or more appliances can be held on the support rail in such a way that they can be moved along the support rail without using tools and with only a slight force being applied. For this purpose, one or more slide bearings and/or roller bearings can be provided between an appliance and the support rail, for example on a trolley. Alternatively, the one or more appliances can be held on the support rail in such a way that the positions of the appliances can be changed only by using tools and/or by applying considerable force.

The arc-shaped support rail can allow the position or positions of appliances to be individually adapted to the requirements of different medical activities and/or to the needs and habits of different medical personnel.

The support rail is arranged in particular in a horizontal plane above and at a distance from the storage units.

In a medical workstation with a transport rail, as it is described here, the support rail has in particular at least one portion in the shape of an arc of a circle with a center point at or over the position provided for medical personnel.

A design of the support rail in the shape of an arc of a circle is not only esthetically advantageous, in combination with the arrangement of the storage units in an arc of a circle, but first and foremost also affords the possibility of substantially adapting the medical workstation to different requirements, habits and needs.

In a medical workstation with a support rail, as it is described here, the support rail has in particular a channel for receiving a cable or a hose.

The channel can have a cross section that is continuously open or that is closed in some areas, and it can be designed to receive one or more cables and/or hoses. If cables and/or hoses for supplying appliances held by the support rail with electrical and/or optical signals, power, compressed air or other fluids are arranged in the channel, this can simplify the installation of the appliances and give a clean and neat appearance.

In a medical workstation with a support rail having a channel, as it is described here, the support rail has in particular an upwardly open U-shaped cross section, wherein the interior of the cross section of the support rail forms the channel.

In a medical workstation, as it is described here, a storage unit has in particular a trunk with a bottom plate in the form of a segment of a circular ring and non-parallel side walls and, in the trunk, an insert for receiving an object, wherein the insert has parallel side walls.

A segment of a circular ring has an edge with two portions in the shape of an arc of a circle and with two straight portions, wherein the arcs are parts of two concentric circles and the straight line are radii of these circles. The trunk can also have a curved rear wall, in particular a rear wall in the shape of a cutout of a circular cylindrical jacket. The insert comprises in particular one or more open compartments, one or more drawer units each with one or more drawers, one or more bins for placing unsterile instruments or used disposable items, and/or one or more instrument compartment units. The insert can be designed to receive several articles that are of different size and have different functions and other properties.

In a medical workstation with a trunk, and with an insert in the trunk, as it is described here, the insert comprises in particular a pull-out.

BRIEF DESCRIPTION OF THE DRAWINGS

Embodiments are explained in more detail below with reference to the attached figures, where.

DETAILED DESCRIPTION OF THE INVENTION

Figure 1:
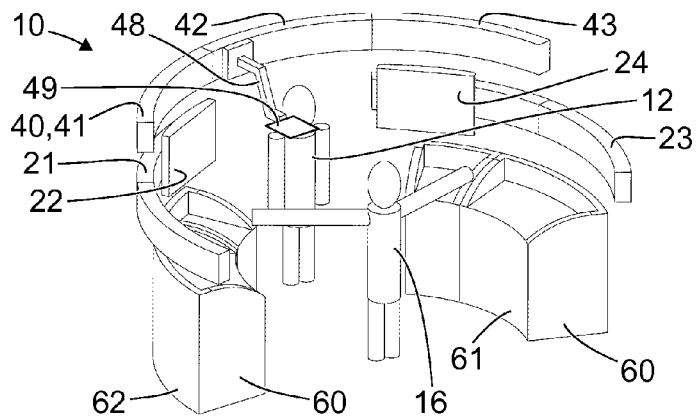
FIG. 1 shows a schematic view of a medical workstation.

FIG. 1 shows a schematic axonometric view of a medical workstation 10 for a patient 12 and medical personnel 16, in particular a doctor. The patient 12 and the medical personnel 16 are each shown at the positions provided for them. In a departure from the view in FIG. 1, the patient 12 can be seated or lying down and/or the medical personnel 16 can be seated. In the text below, reference sign 12 is used both for the patient and also for the positions provided for the patient during a medical activity performed on the patient by the medical personnel. Moreover, reference sign 16 is used both for the medical personnel and also for the positions provided for the medical personnel during a medical activity performed on the patient by the medical personnel.

The medical workstation 10 comprises a first support rail 21 in the shape of an arc of a circle, and a second support rail 23 in the shape of an arc of a circle. The support rails 21, 23 in the shapes of an arc of a circle are arranged such that the center points of their curvature are located at or vertically above the position provided for medical personnel 16. The support rails 21, 23 are arranged on both sides of the position provided for the patient 12. The support rails 21, 23 are arranged in a horizontal plane.

A first display screen 22 is held by the first support rail 21 and is movable along the first support rail 21. A second display screen 24 is held by the second support rail 23 and is movable along the latter. Alternatively or in addition, further appliances, in particular medical appliances, can be held and moved on each of the support rails 21, 23.

Slide bearings or roller bearings, which allow movement with minimal force, can be provided between the support rails 21, 23, on the one hand, and the display screens 22, 24 or other appliances held on the support rails 21, 23, on the other hand. Alternatively, the display screens 22, 24 and/or other appliances can be held on the support rails 21, 23 in such a way that they are each movable along the support rails 21, 23 only by applying considerable force and/or using tools. Moreover, the support rails 21, 23 can be designed in such a way that the display screens 22, 24 and/or other appliances can be arranged, in particular suspended, only at a predetermined number of discrete positions spaced apart from one another.

Moreover, the medical workstation 10 comprises a transport rail 40 with a loading area 41 to the left of the patient 12 (as seen from the medical personnel 16), a use area 42 near the patient 12, and an unloading area 43 to the right of the patient 12. The loading area 41 and unloading area 43 can be interchanged. Alternatively, both areas 41, 43 can be provided both for loading and also for unloading. The transport rail 40 is arranged in a horizontal plane above the support rails 21, 23.

A holding arm 48 for an instrument carrier 49 is held by the transport rail 40 and is movable along the latter. For this purpose, one or more slide bearings and/or roller bearings are provided between the transport rail 40 and the holding arm 48.

The tray-shaped instrument carrier 49 in the example shown can be loaded, for example with sterile instruments and/or disposable items, in the loading area 41 and, when needed, can be moved into the use area 42 near the patient 12. After the instruments made available on the instrument carrier 49 on the holding arm 48 have been used in the context of a medical activity, the holding arm 48 with the instrument carrier 49 can be moved into the unloading area 43 of the transport rail. Since the loading area 41 and the unloading area 43 are at a distance from the use area 42 and from the patient 12, a first instrument carrier can be loaded or equipped in the loading area 41 while at the same time a second instrument carrier is unloaded or emptied in the unloading area 43, without adversely affecting a medical activity performed on the patient 12 by the medical personnel 16 (in particular using instruments that are made available on a third instrument carrier in the use area 42).

Storage units 60 are provided substantially under the horizontal planes in which the support rails 21, 23 and the transport rail 40 are arranged. The storage units 60 are arranged in the shape of an arc of a circle. The position 12 provided for a patient is likewise arranged in the arc of a circle formed by the storage units 60. In addition to the storage units 60, it is possible for appliances, in particular cabinet-shaped appliances, to be arranged in the same arc of a circle. The center point of the arc of a circle lies at the position 16 provided for the medical personnel.

The individual storage unit 60 has in particular the shape of a segment of an arc of a circle. In particular, the individual storage unit 60 has a front face 61 and a rear wall 62 in the form of two cutouts of circular cylindrical jackets. The storage units 60 are arranged such that the position 16 provided for medical personnel lies on the common vertical axis of symmetry of the circular cylindrical jackets, of which the cutouts form the front faces 61 and the rear walls 62.

Figure 2:
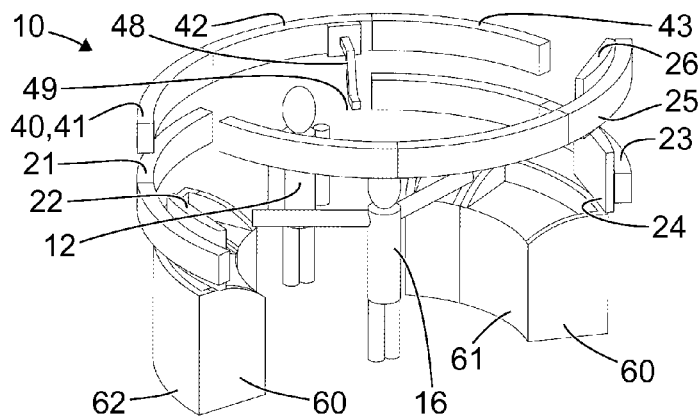
FIG. 2 shows a schematic view of another medical workstation.

FIG. 2 shows a schematic axonometric view of another medical workstation 10 which, in some features and properties, is similar to the medical workstation shown above in FIG. 1. It is basically only those features and properties in which the medical workstation 10 differs from the one shown in FIG. 1 that are described below.

The medical workstation 10 comprises a third support rail 25. A third display screen 26 is held by the third support rail 25 and is movable along the latter. The third support rail 25 is in particular arranged such that, during a medical activity performed on the patient 12, the third display screen 26 lies in the field of view of said patient. To prevent the third display screen 26 from being concealed by the medical personnel 16, the third display screen 26 can be moved along the third support rail 25. The third display screen 26 can be used, for example, to present a film or other material that relaxes the patient 12, or it can allow the patient 12 to follow the course of a medical procedure.

To illustrate the mobility of the display screens 22, 24 along the support rails 21, 23, the display screens 22, 24 are arranged at positions that are further from the patient 12 than is shown in FIG. 1. The first display screen 22 on the first support rail 21 and the second display screen 24 on the second support rail 23 are, for example, moved to the positions shown in FIG. 2 when they are not needed for the current medical activity.

Figure 3:
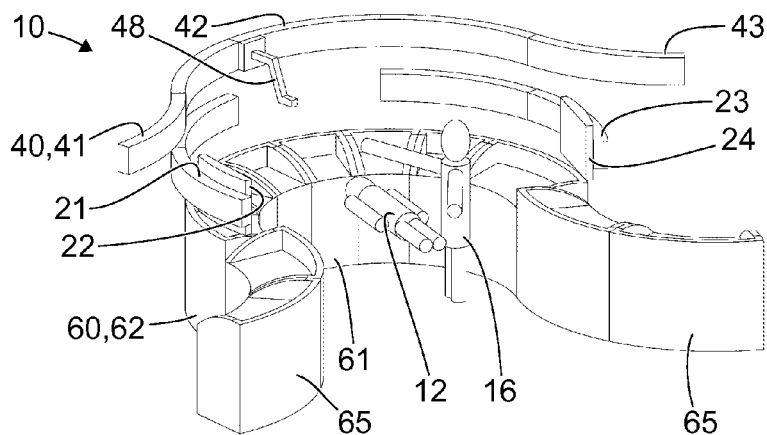
FIG. 3 shows a schematic view of another medical workstation.

FIG. 3 shows a schematic axonometric view of another medical workstation 10 which, in some features and properties, is similar to the medical workstations shown above in FIGS. 1 and 2. It is basically only those features and properties in which the medical workstation 10 differs from the ones shown in FIGS. 1 and 2 that are described below.

The medical workstation 10 differs from the medical workstations shown above in FIGS. 1 and 2 in that, among other things, the position provided for the patient 12 does not lie between the storage units 60 and form an arc of a circle together with these. Instead, the storage units 60 form a completely or substantially closed semicircular arc, and the patient 12 is arranged in the interior of this arc.

Moreover, the medical workstation 10 shown in FIG. 3 differs from the medical workstations shown in FIGS. 1 and 2 in that the two ends of a central and substantially semicircular arrangement of storage units 60 are adjoined by further storage units 65, which form arcs that are curved in the opposite direction or outwards. These further storage units 65 can be used, for example, in the work carried out before and after medical activities.

Moreover, the medical workstation 10 shown in FIG. 3 differs from the ones shown in FIGS. 1 and 2 in that the transport rail 40 is continued at both ends in the form of arcs of opposite curvature. In particular, the loading area 41 and the unloading area 43 of the transport rail 40 are arranged over the further storage units 65. Corresponding to the opposite curvature of the arrangement of the further storage units 65, the loading area 41 and the unloading area 43 have curvatures opposite to that of the use area 42.

Figure 4:
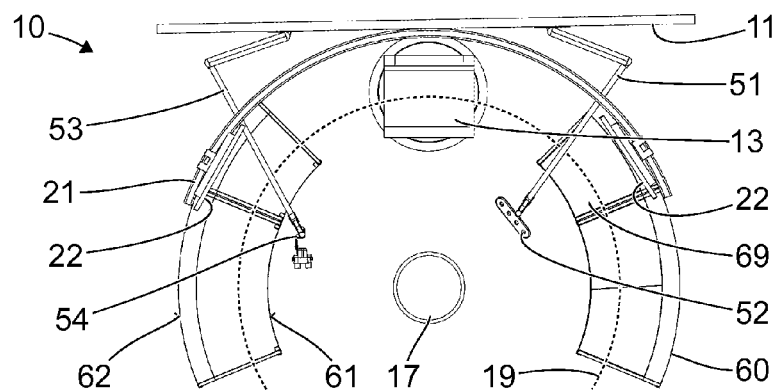
FIG. 4 shows a schematic view of another medical workstation.
Figure 5:
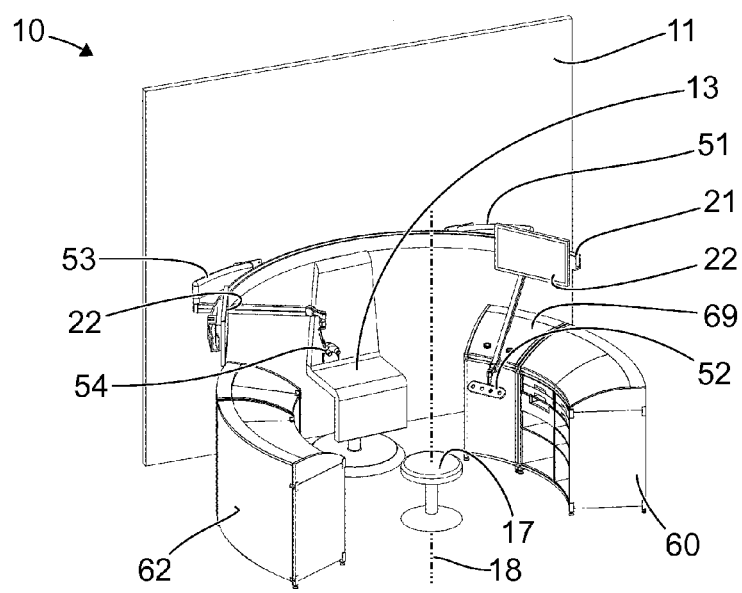
FIG. 5 shows another schematic view of the medical workstation from FIG. 4.
Figure 6:
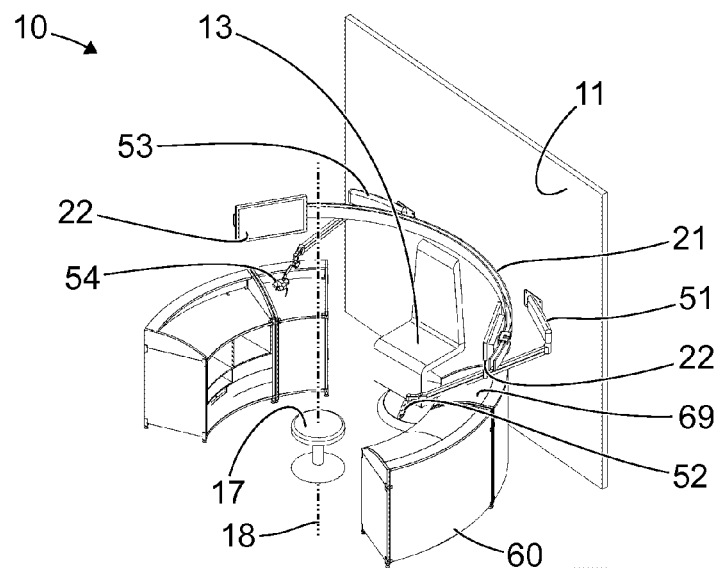
FIG. 6 shows another schematic view of the medical workstation from FIGS. 4 and 5.

FIG. 4 shows a schematic plan view of another medical workstation 10 which, in some features and properties, is similar to the medical workstations shown above in FIGS. 1 to 3. FIG. 5 shows a schematic axonometric view of the medical workstation from FIG. 4. FIG. 6 shows another schematic axonometric view of the medical workstation from FIGS. 4 and 5. It is basically only those features and properties in which the medical workstation 10 differs from the ones shown in FIGS. 1 to 3 that are described below.

In the medical workstation 10 shown in FIGS. 4, 5 and 6, the position provided for a patient is defined by a treatment chair 13, and the position provided for medical personnel is defined by a seat 17, in particular a stool. In the same way as in the medical workstations shown above in FIGS. 1 and 2, the position 12 provided for a patient forms, together with storage units 60, an arc of a circle which, in the plan view in FIG. 4, is indicated by a broken line. FIGS. 5 and 6 indicate the vertical axis of symmetry 18 of the circular cylindrical jacket shaped front faces 61 and rear faces 62 of the storage units 60.

The medical workstation 10 shown in FIGS. 4 to 6 also differs from the medical workstations shown above in FIGS. 1 and 2 in that only one support rail 21 is provided on which, for example, two display screens 22 are held so as to be movable thereon. A transport rail for an instrument carrier, as shown in FIGS. 1 to 3, is not provided, but can be added.

Moreover, the medical workstation 10 shown in FIGS. 4 to 6 differs from the medical workstations shown in FIGS. 1 and 2 in that holding arms 51, 53, which hold instrument carriers 52, 54, are articulated on a room wall 11.

Moreover, the medical workstation 10 shown in FIGS. 4 to 6 differs from the ones shown in FIGS. 1 and 2 in that the arc of a circle 19 (cf. FIG. 4) is formed not only by storage units 60 and the treatment chair 13, but also by a cabinet-shaped medical appliance 69. The cabinet-shaped medical appliance 69 contains, for example, a control unit, an electrical power supply, a light source and/or supply devices for providing compressed air or other fluids for dental instruments or for an endoscope and/or other medical instruments for microinvasive procedures.

Figure 7:
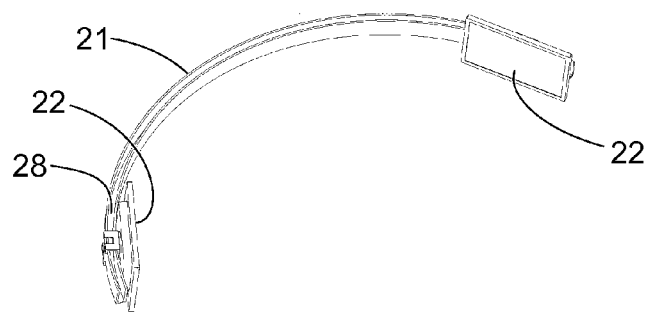
FIG. 7 shows a schematic view of a support rail.

FIG. 7 shows a schematic axonometric view of a support rail 21 with two display screens 22. The support rail 21 is in particular one of the support rails of the medical workstations from FIGS. 1 to 6.

The support rail 21 has an upwardly open U-shaped cross section, of which the interior forms a cable channel 28. Cables for the electrical power supply of the display screens 22 or of other appliances held by the support rail 21, and electrical and/or optical signal lines and fluid lines to the display screens 22 or to other appliances, can be arranged in the cable channel 28.

Figure 8:
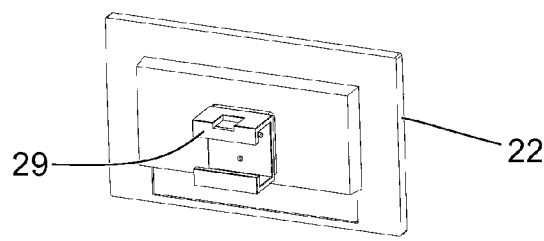
FIG. 8 shows a schematic view of an appliance.

FIG. 8 shows a schematic axonometric view of the rear of a display screen 22. On the rear of the display screen 22, a fastening mechanism 29 is provided by means of which the display screen 22 can be held on a support rail 21, 23, 25 (cf. FIGS. 1 to 7). In particular, the fastening mechanism 29 is C-shaped in order to engage the support rail 21, 23, 25 from above and below or from behind. The materials of the fastening mechanism 29 and of the support rails 21, 23, 25 can be provided to permit easy sliding along the support rails 21, 23, 25. Alternatively, slide bearings or roller bearings (not shown in FIG. 8) are provided for this purpose.

Figure 9:
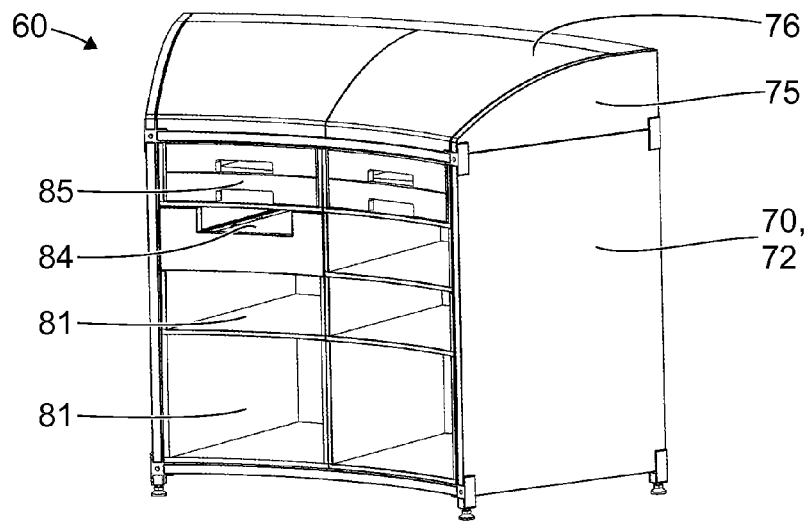
FIG. 9 shows a schematic view of a storage unit.

FIG. 9 shows a schematic axonometric view of a storage unit 60 that can be used at the medical workstations 10 from FIGS. 1 to 6. The storage unit 60 has a trunk 70, of which FIG. 9 shows mainly a large rectangular lower side wall 72 and a smaller upper side wall 75, and also an upper cover 76. The trunk 70 has basically the shape of a segment of an arc of a circle, the side walls 72, 75 being in particular arranged radially.

Several inserts 81, 84, 85, which are explained below with reference to FIGS. 12 to 16, are arranged in the trunk 70.

Figure 10:
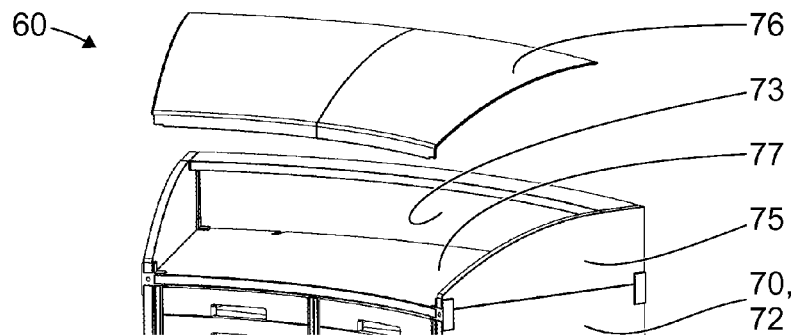
FIG. 10 shows another schematic view of the storage unit from FIG. 9.

FIG. 10 shows another schematic axonometric view of an upper area of the trunk 70 from FIG. 9. The upper cover 76 is convex and in particular has the shape of a cutout of a surface of a torus. The upper cover 76 shown in FIG. 10 is offset vertically upwards as in an exploded view. The cover 76 can be connected to a rear wall 73 of the trunk 70 by means of one or more hinges or joints. Alternatively, the upper cover 76 can be moved horizontally on a rail or can be lifted vertically by means of a lifting mechanism. Under the upper cover 76, a placement surface 77 is provided, for example for medical instruments, disposable items, patient files or other documents.

Figure 11:
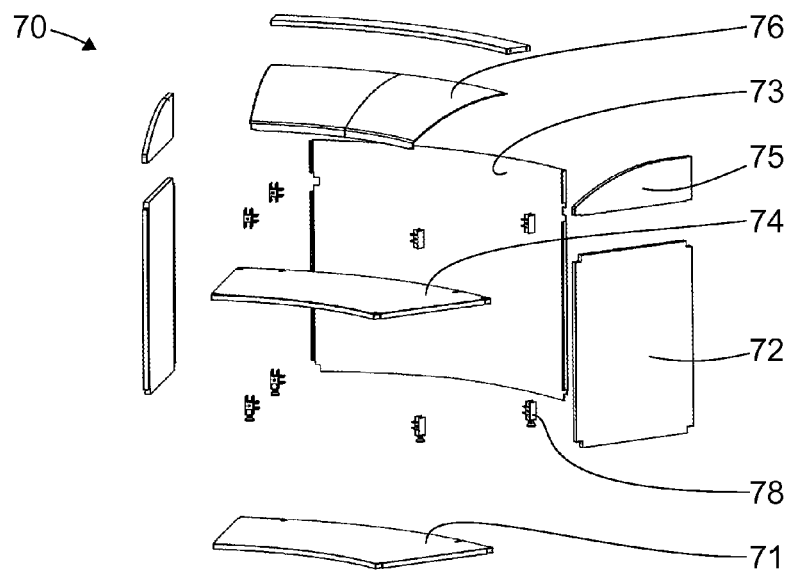
FIG. 11 shows a schematic view of component parts of the storage unit from FIGS. 9 and 10.

FIG. 11 shows another schematic axonometric view of the trunk 70 from FIGS. 9 and 10. Individual component parts of the trunk 70 are shown offset vertically and/or horizontally relative to each other as in an exploded view, but still in the intended spatial orientation. A bottom plate 71 and a compartment bottom 74, which forms the placement surface 77 (cf. FIG. 10), each have the shape of a segment of an arc of a circle with two straight, radially extending edge portions and with two concentrically arranged edge portions that each have the shape of an arc of a circle. The rear wall 73, at least in the assembled state, is in the form of a cutout of a circular cylindrical jacket. The side walls 72, 75 are oriented vertically and radially.

The bottom plate 71, side walls 72, 75, rear wall 73 and compartment bottom 74 are rigidly mechanically connected by connectors 78. The connectors 78 are, for example, connectors sold by Stork GmbH & Co KG, Marienfeld, Germany, under the brand name CONEX19.

Figure 12:
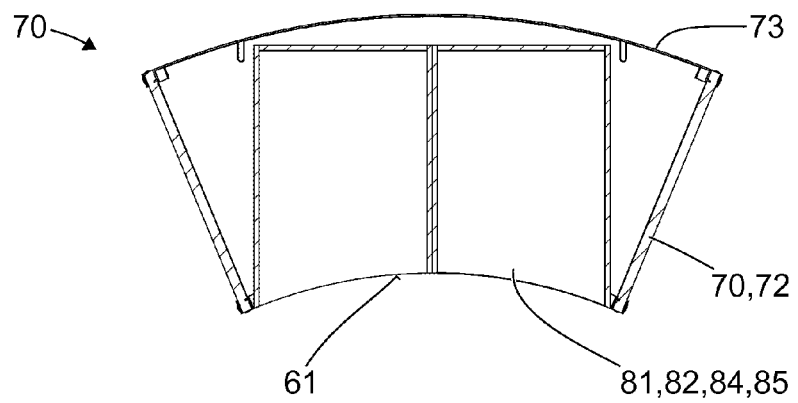
FIG. 12 shows another schematic view of the storage unit from FIGS. 9 to 11.

FIG. 12 shows a schematic view of a section along a horizontal plane through the storage unit 60 from FIG. 9. The outline of the trunk 70 in the shape of a segment of an arc of a circle can be seen in FIG. 12. Straight and radial edges of the outline are formed by the side walls 72. Concentric edges in the shape of arcs of a circle are formed by the front face 61 and the rear wall 73. As can already be seen from FIG. 9, the front face 61 does not have to be a continuous, closed surface as in FIGS. 1 to 3, and instead it can have openings or be partially or completely open.

FIG. 12 also shows the outlines of the inserts 81, 82, 84, 85 shown in FIG. 9 and arranged in the trunk 70. In contrast to the trunk 70, the inserts 81, 82, 84, 85 have outlines with parallel straight sides and with a straight rear face orthogonal to the sides. Only the fronts of the contours of the inserts 81, 82, 84, 85 are shaped like an arc of a circle and are adapted to or form the front face 61 of the storage unit.

Figure 13:
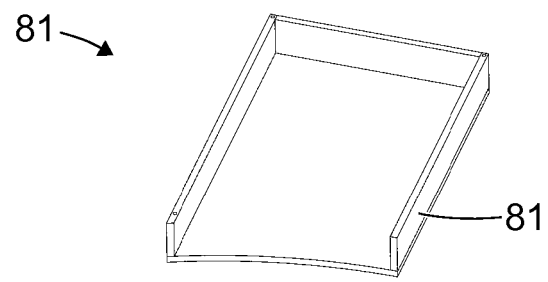
FIG. 13 shows a schematic view of an insert for a storage unit.

FIG. 13 shows a schematic axonometric view of a first insert 81 in the form of a compartment that is open at the front and at the top and which has parallel and plane side walls 86.

Figure 14:
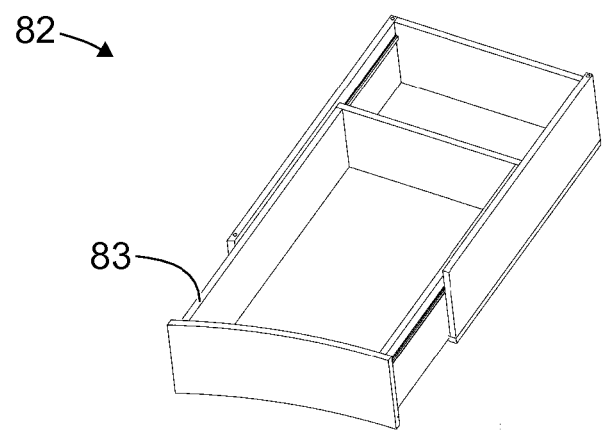
FIG. 14 shows a schematic view of another insert for a storage unit.

FIG. 14 shows a schematic axonometric view of another insert in the form of a drawer unit 82 with a pull-out drawer 83 between likewise parallel and plane side walls.

Figure 15:
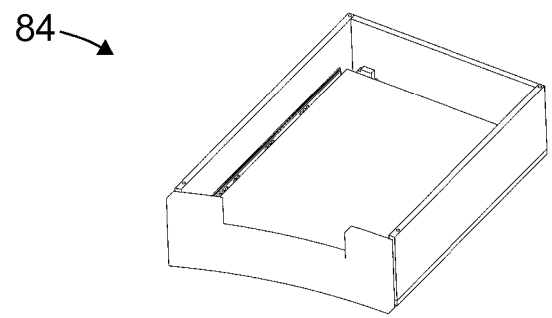
FIG. 15 shows a schematic view of another insert for a storage unit.

FIG. 15 shows a schematic axonometric view of another insert in the form of a waste receptacle 84 with parallel and plane side walls. The waste receptacle 84 is substantially but not completely closed at the front, in order to allow used and unsterile instruments or used disposable items to be discarded in the waste receptacle 84.

Figure 16:
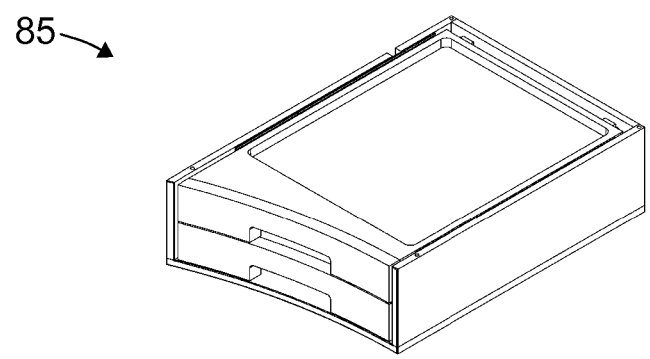
FIG. 16 shows a schematic view of another storage unit.

FIG. 16 shows a schematic axonometric view of an instrument compartment unit 85 with two parallel side walls 86. The instrument compartment unit 85 has two drawers which are arranged one over the other and, like the drawer unit 82 from FIG. 14, can be pulled out forwards independently of each other.

It will be seen in FIGS. 13 to 16 that all the inserts 81, 82, 84, 85 have fronts, in particular suitable curved edges or screens, that are adapted to the curved front face 61 (cf. FIGS. 1 to 4 and 12).

Figure 17:
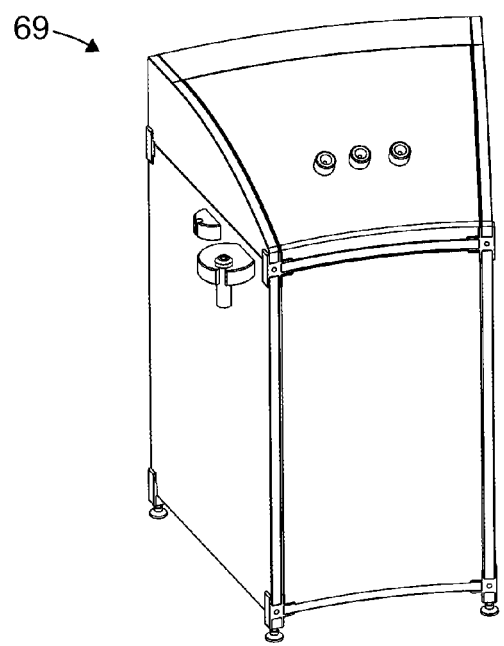
FIG. 17 shows a schematic view of a cabinet-shaped appliance.

FIG. 17 shows a schematic axonometric view of a cabinet-shaped medical appliance 69, as can be used in the illustrative embodiment in FIGS. 4 to 6.

Figure 18:
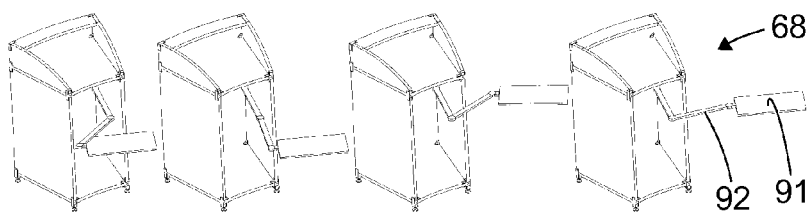
FIG. 18 shows a schematic view of another storage unit.

FIG. 18 shows four different schematic axonometric views of a storage unit 68 optimized for a computer. A keyboard mount 91 is connected to the storage unit 68 via a support arm 92 with several joints, in such a way that the keyboard mount 91 can be positioned freely within wide limits. Four different possible positions of the keyboard mount 91 are shown in FIG. 18.

LIST OF REFERENCE SIGNS 10 medical workstation
11 room wall 12 patient
13 treatment chair for patient 12
16 medical personnel
17 seat for medical personnel 16
18 axis of symmetry
19 arc of a circle
21 first support rail
22 first display screen on first support rail 21
23 second support rail
24 second display screen on second support rail 23
25 third support rail
26 third display screen on third support rail 25
28 cable channel in support rail 21, 23, 25
29 fastening mechanism
40 transport rail
41 loading area of transport rail 40
42 use area of transport rail 40
43 unloading area of transport rail 40
48 holding arm (for instrument carrier 49) movable on support rail 40
49 instrument carrier on holding arm 48
51 holding arm
52 instrument carrier
53 holding arm
54 instrument carrier
60 storage unit
61 front face of storage unit 60
62 rear face of storage unit 60
65 further storage unit
68 storage unit for computer
69 cabinet-shaped medical appliance
70 trunk
71 bottom plate of trunk 70
72 lower side wall of trunk 70
73 rear wall of trunk 70
74 compartment bottom of trunk 70
75 upper side wall of trunk 70
76 upper cover of trunk 70
77 placement surface under the upper cover 76
78 connector
81 open compartment
82 drawer unit
83 pull-out drawer of the drawer unit
84 waste receptacle
85 instrument compartment unit
86 side wall
91 keyboard mount
92 support arm for keyboard mount 91

The invention claimed is:

1. A medical workstation with:
storage units for receiving medical instruments or tools, the storage units arranged in a shape of an arc of a circle around a first position provided for medical personnel, the arc defining a uses area that is between 1.5 and 2 meters in diameter,
a transport rail holding an instrument carrier that is movable along the transport rail in the use area, the transport rail having a loading area at a first end and an unloading area at a second end, the loading area and the unloading area both outside of the use area,
an arc-shaped support rail holding an appliance movable along the support rail, in which the support rail has at least one portion in a shape of an arc of a circle with a center point at or over the first position; wherein the support rail has an upwardly open U-shaped cross section, wherein an interior of the U-shaped cross section of the support rail forms a channel for receiving a cable or hose.

2. The medical workstation according to claim 1, in which the transport rail is arranged in a horizontal plane above and at a distance from the storage units.

3. The medical workstation according to claim 1, in which a second position provided for a patient during a medical activity is arranged in the arc of a circle formed by the storage units.

4. The medical workstation according to claim 1, in which one of the storage units has a trunk with a bottom plate in the form of a segment of a circular ring and non-parallel side walls and, in the trunk, an insert for receiving an object, wherein the insert has parallel side walls.

5. The medical workstation according to claim 4, in which the insert comprises a pull-out.

6. The medical workstation according to claim 1, wherein the transport rail has at least one portion in the shape of an arc of a circle with a center point at or over the first position and ends of the transport rail form arcs of opposite curvature.

7. The medical workstation according to claim 6, wherein the at least one portion of the transport rail is in the shape of a semi-circle.

8. The medical workstation according to claim 1, wherein the support rail comprises two disconnected support rails at least partially on either side of the first position.

9. The medical workstation according to claim 1, wherein the support rail is in the shape of a semi-circle corresponding with the shape of the use area.

10. The medical workstation according to claim 1, wherein the transport rail is on a room wall.

11. The medical workstation according to claim 1, wherein the storage units have a cylindrical jacket surface with a diameter between 1.5 and 2 meters.

12. The medical workstation according to claim 1, wherein one or more bearings are provided between the appliance and the support rail.

13. The medical workstation according to claim 1, wherein the appliance comprises a display screen.

14. The medical workstation according to claim 1, wherein one or more bearings are provided between the instrument carrier and the transport rail.

15. The medical workstation according to claim 1, wherein one of the storage units comprises a cabinet-shaped medical appliance having an arc-shaped perimeter corresponding with the shape of the arc of the circle around the first position.

16. The medical workstation according to claim 1, wherein the support rail is adapted to have at least discrete positions spaced apart from one another where the appliance can be positioned.

17. The medical workstation according to claim 1, wherein the medical workstation is adapted such that only an area or body part of patient that is to be operated on is located in the use area.

18. A medical workstation comprising:
storage units for receiving medical instruments or tools, the storage units arranged in a shape of an arc of a circle around a first position provided for medical personnel, the arc defining a use area that is between 1.5 and 2 meters in diameter,
a transport rail holding an instrument carrier that is movable along the transport rail in the use area, the transport rail having a loading area at a first end and an unloading area at a second end, the loading area and the unloading area both outside of the use area, the transport rail having at least one portion in a shape of an arc of a circle with a center point at or over the first position and ends of the transport rail form arcs of opposite curvature, an arc-shaped support rail holding an appliance movable along the support rail, the support rail having at least one portion in a shape of an arc of a circle with a center point at or over the first position, the support rail adapted to have at least four discrete positions spaced apart from one another where the appliance can be positioned.

* * * * *